(12) United States Patent
Carreira et al.

(10) Patent No.: US 12,377,128 B2
(45) Date of Patent: *Aug. 5, 2025

(54) USE OF CHELATING AGENT AND PEPTIDE ANTIMICROBIAL COMPOUNDS

(71) Applicants: Alexandra Carreira, Cantanhede (PT); Sara Valadas Da Silva Monteiro, Cantanhede (PT); Ricardo De Seixas Boavida Ferreira, Cantanhede (PT)

(72) Inventors: Alexandra Carreira, Cantanhede (PT); Sara Valadas Da Silva Monteiro, Cantanhede (PT); Ricardo De Seixas Boavida Ferreira, Cantanhede (PT)

(73) Assignee: Consumo Em Verde Biotecnologia Das Plantas, S.A., Cantanhede (PT)

( * ) Notice: Subject to any disclaimer, the term of this patent is extended or adjusted under 35 U.S.C. 154(b) by 36 days.

This patent is subject to a terminal disclaimer.

(21) Appl. No.: 17/485,345

(22) Filed: Sep. 25, 2021

(65) Prior Publication Data
US 2022/0000970 A1    Jan. 6, 2022

Related U.S. Application Data

(63) Continuation of application No. 16/278,056, filed on Feb. 16, 2019, now Pat. No. 11,154,588, which is a continuation of application No. 13/879,169, filed as application No. PCT/EP2011/067828 on Oct. 12, 2011, now Pat. No. 10,265,376.

(30) Foreign Application Priority Data

Oct. 12, 2010  (PT) .......................... 105332
Oct. 13, 2010  (GB) ..................... 1017282

(51) Int. Cl.
*A61K 38/16* (2006.01)
*A01N 37/44* (2006.01)
*A01N 65/20* (2009.01)

(52) U.S. Cl.
CPC .............. *A61K 38/16* (2013.01); *A01N 37/44* (2013.01); *A01N 65/20* (2013.01)

(58) Field of Classification Search
None
See application file for complete search history.

(56) References Cited

U.S. PATENT DOCUMENTS

| | | | |
|---|---|---|---|
| 9,095,166 B2 * | 8/2015 | Valadas Da Silva Monteiro | A21D 2/267 |
| 9,402,404 B2 * | 8/2016 | Carreira | A23L 3/34635 |
| 10,265,376 B2 * | 4/2019 | Carreira | A01N 37/44 |
| 11,154,588 B2 * | 10/2021 | Carreira | A01N 65/20 |
| 2004/0138176 A1 * | 7/2004 | Miles | A01N 25/00 514/343 |
| 2008/0300137 A1 * | 12/2008 | De Seixas Boavida Ferreira | C07K 14/415 536/23.6 |

FOREIGN PATENT DOCUMENTS

WO    WO 93/11783    *    6/1993

OTHER PUBLICATIONS

John M Wells et al: "In vitro Inhibition of Soft-Rotting Bacteria by EDTA and Nisin and in vivo Response on Inoculated Fresh Cut Carrots", Plant Disease, Jan. 1, 1998 (Jan. 1, 1998 ), pp. 491-495, XP55014413, Retrieved from the Internet: U RL:http://apsjournals.apsnet.org/doi/pdf/10.1094/PDIS.1998.82.5.491 [retr.*
Arun K Chatterjee et al: "Unusual Susceptibility of Erwinia amylovora to Antibacterial Agents in Relation to the Barrier Function of its Cell Envelope", Antimicrobial Agents and Chemotherapy, May 1, 1977 (May 1, 1977 ), pp. 897-905, XP55014414, Retrieved from the Internet: U RL:http://www.ncbi.nlm.nih .gov/pmc/art.*
Haque H et al: "Cell Envelopes of Gram Negative Bacteria: Composition, Response To Chelating Agents and Susceptibility of Whole Cells To Antibacterial Agents", Journal of Applied Bacteriology, Blackwell Publishing Ltd., Oxford, GB, vol. 40, No. 1,Jan. 1, 1976 (Jan. 1, 1976 ), pp. 89-99, XP009048176, ISSN: 0021-8.*

* cited by examiner

*Primary Examiner* — Maury A Audet
(74) *Attorney, Agent, or Firm* — Adam Warwick Bell; Matthew Rupert Kaser

(57) ABSTRACT

The inventors provide the use of a chelating agent and an antimicrobial agent that is effective against a plant pathogenic microorganism to inhibit the growth of and/or kill a plant pathogenic microorganism on a plant; the use of a chelating agent to increase the activity of an antimicrobial that is effective against a plant pathogenic microorganism; a method of inhibiting the growth of and/or killing a plant pathogenic microorganism comprising administering to a plant in need thereof a chelating agent and an antimicrobial agent that is effective against a plant pathogenic microorganism; and a method of increasing the activity of an antimicrobial that is effective against a plant pathogenic microorganism comprising using said antimicrobial with a chelating agent. Also provided is a composition comprising a chelating agent and an antimicrobial agent that is effective against a plant pathogenic microorganism, use of said composition to inhibit the growth of and/or kill a plant pathogenic microorganism on a plant, and a method of inhibiting the growth of and/or killing a plant pathogenic microorganism comprising administering to a plant in need thereof said composition. Further provided is the use of a composition comprising an antimicrobial polypeptide comprising Blad or an active variant thereof to kill, or inhibit the growth of, a plant pathogenic bacterium on a plant, and a method of killing, or inhibiting the growth of, a plant pathogenic bacterium on a plant, said method comprising administering to said plant a composition comprising an effective amount of an antimicrobial polypeptide comprising Blad or an active variant thereof.

2 Claims, 2 Drawing Sheets

Specification includes a Sequence Listing.

Figure 1

```
   1 gatggcgatg aatgaacact gcgtttgctg gctttgatga aaatcgagtg caacctaata
  61 taatcaaata tgggtaagat gagagtgagg tttccaacgt tagtgttggt actaggaata
 121 gtattcctca tggcagtgtc aattggtatt gcttatggag aaaagatgt gctaaagagt
 181 catgagaggc ctgaggaaag agaacaagag gagtggcaac ctaggagaca acgacctcaa
 241 agtagaaggg aagagagaga gcaagagcaa gagcagggtt ctccctcata cccacgcagg
 301 cagagtggtt atgagaggag acaataccat gagaggagtg agcagaggga agagagagag
 361 caagaacaac aacaaggttc tccctcatac tcacgtagac aaaggaaccc ttatcacttc
 421 agctctcaaa gattccaaac tctttacaaa aataggaatg gcaaaatccg tgtgctcgag
 481 aggtttgacc aaagaaccaa tagacttgag aatctccaaa actaccgcat tgttgagttc
 541 caatcaaaac ctaacactct cattctccct aaacactctg atgctgacta cgtcctcgtt
 601 gtactcaatg gtagagccac aatcacgata gtaaacactg atagaagaca agcatataac
 661 cttgagtatg gcgatgctct cagaatccca gctggctcaa cttcatatat ccttaacccg
 721 gatgacaacc agaagcttag agtagtcaag ctcgcaatac ccatcaacaa tcctggctac
 781 ttttatgatt tctatccatc gagtactaaa gaccaacaat cctacttcag tggcttcagc
 841 aggaacactt tagaggccac cttcaatact cgttatgaag agatacaaag gattatttta
 901 gggaatgagg atgagcaaga atatgaggaa caaaggcgtg ggcaagagca gagcgaccaa
 961 gacgaggggg tgatagtgat agtttcaaag aaacagatcc aaaaattgac aaaacacgct
1021 caatcttcat caggaaaaga caaaccctct gattctggcc ccttcaactt gagaagcaat
1081 gagcccatat attcaaacaa gtatgggaac ttctatgaaa tcactccaga tagaaaccct
1141 caagttcagg atttgaatat ctctctcacc tatataaaaa ttaacgaggg agctttgttg
1201 ttgccacact ataactcaaa ggccatatat gtagtcgtgg ttgatgaagg agaaggaaat
1261 tatgaactgg taggtattcg agatcaacaa cgacaacaag atgagcaaga agagaaagag
1321 gaagaagtga taaggtatag tgctagatta tcagaaggtg acatttttgt aattccagca
1381 ggttatccaa tttccatcaa tgcttcctca aatcttcgct tgcttggatt tggcatcaat
1441 gctgatgaaa accagaggaa ttcctcgca ggttctaaag acaatgtgat aaggcagtta
1501 gatagagcag tgaatgagct cacattccct ggttctgctg aagatattga gagattaatc
1561 aaaaaccaac aacagtctta ctttgcaaat ggtcagcctc aacaacaaca acaacaacaa
1621 agtgagaagg agggaaggcg tggaagaagg ggttcatctc ttccatttg agcactttt
1681 actaagctgt tttaaaagct actatcatgt aagagctcat agtgagctac tgagagaata
1741 ataaaactaa agttggacct ttgtactaat aatgttaata aaaaaaaaa a
```

Figure 2

```
  1 cgtagacaaa ggaacccttc tcacttcagc tctcaaagat tccaaactct ttacaaaaat
 61 aggaatggca aaatccgtgt gctcgagagg tttgaccaaa gaaccaatag acttgagaat
121 ctccaaaact accgcattgt tgagttccaa tcaaaaccta acactctcat tctccctaaa
181 cactctgatg ctgactacgt cctcgttgta ctcaatggta gagccacaat cacgatagta
241 aaccctgata gaagacaagc atataaacctt gagtatggcg atgctctcag aatcccagct
301 ggctcaactt catatatcct taacccggat gacaaccaga agcttagagt agtcaagctc
361 gcaataccca tcaacaatcc tggctacttt tatgatttct atccatcgag tactaaagac
421 caacaatcct acttcagtgg cttcagcagg aacactttag aggccaccttt caatactcgt
481 tatgaagaga tacaaaggat tatttaggg aatgaggat
```

USE OF CHELATING AGENT AND PEPTIDE ANTIMICROBIAL COMPOUNDS

A sequence listing text (.txt) file is submitted herewith under 37 CFR. 1.821 (c) and is transferred from PCT/EP2011/067828 under 37 CFR 1.821 (e), and is hereby incorporated by reference in its entirety. The details of the file as required under 37 CFR. 1.52 (e) (5) and 37 CFR 1.77 (b) (5) are as follows: Name of file is P11337_WO_ST25.txt; date of creation/modification is Monday, Apr. 8, 2013, 8:54:00 PM. The information recorded in electronic form (if any) submitted (under Rule 13ter if appropriate) with this application is identical to the sequence listing as contained in the application as filed.

FIELD OF THE INVENTION

The invention relates to the field of antimicrobial agents that target plant pathogens.

INTRODUCTION

The control of plant pathogens and the protection of crops is a serious worldwide issue that is becoming an increasing concern with recent increases in the world's population and the associated food shortages. In addition, modern agriculture practices in relation to harvest and storage tend to provide good conditions for pathogen growth.

The use of chemical pesticides has been the standard approach to pest control. However, many currently used pesticides display several serious disadvantages. For example, many have an adverse impact on the environment and many have low or decreasing efficacy. Of particular concern are the low potency and/or narrow spectrum of activity of some compounds, together with the development of pathogen resistance.

It is among the objectives of the present invention to attempt a solution to these problems, and specifically for example to provide a means to improve the activity of antimicrobial agents that are effective against plant pathogenic microorganisms.

SUMMARY OF THE INVENTION

The inventors have surprisingly found that a chelating agent can synergistically potentiate the effectiveness of antimicrobial agents that are effective against a plant pathogenic microorganism.

Accordingly, the inventors provide:
(i) the use of a chelating agent and an antimicrobial agent that is effective against a plant pathogenic microorganism to inhibit the growth of and/or kill a plant pathogenic microorganism on a plant; and
(ii) the use of a chelating agent to increase the activity of an antimicrobial that is effective against a plant pathogenic microorganism.

In preferred embodiments said chelating agent and said antimicrobial are applied to a plant in need thereof, preferably wherein said antimicrobial agent and said chelating agent are administered to said plant:
a) as part of the same composition; or
b) separately, either sequentially or simultaneously.

In preferred embodiments the antimicrobial agent is effective against a plant pathogenic bacterium or fungus. In preferred embodiments the antimicrobial agent comprises a polypeptide, preferably wherein said polypeptide comprises Blad or an active variant thereof. In preferred embodiments the chelating agent is a polyamino carboxylate, preferably EDTA.

The inventors also provide:
a method of inhibiting the growth of and/or killing a plant pathogenic microorganism comprising administering to a plant in need thereof a chelating agent and an antimicrobial agent that is effective against a plant pathogenic microorganism; and
a method of increasing the activity of an antimicrobial that is effective against a plant pathogenic microorganism comprising using said antimicrobial with a chelating agent. Further, the inventors provide a composition comprising a chelating agent and an antimicrobial agent that is effective against a plant pathogenic microorganism. Preferably the antimicrobial agent is effective against a plant pathogenic bacterium or fungus, preferably a fungus. In preferred embodiments the antimicrobial agent comprises a polypeptide, preferably wherein said polypeptide comprises Blad or an active variant thereof. In preferred embodiments the chelating agent is a polyamino carboxylate, preferably EDTA.

The inventors additionally provide the use of a composition of the invention to inhibit the growth of and/or kill a plant pathogenic microorganism on a plant, and a method of inhibiting the growth of and/or killing a plant pathogenic microorganism comprising administering to a plant in need thereof a composition of the invention.

The inventors have also surprisingly found that the Blad polypeptide from *Lupinus* shows potent antimicrobial activity against a number of diverse bacterial organisms that are pathogenic to plants.

Accordingly, the inventors provide the use of a composition comprising an antimicrobial polypeptide comprising Blad or an active variant thereof to kill, or inhibit the growth of, a plant pathogenic bacterium on a plant. Preferably said composition further comprises a chelating agent. In preferred embodiments, said bacterium is a pathogenic species from one of the following genera: *Pseudomonas*, *Erwinia* and *Streptomyces*. In preferred embodiments, the composition is applied to a plant in need thereof.

The inventors also provide a method of killing, or inhibiting the growth of, a plant pathogenic bacterium on a plant, said method comprising administering to said plant a composition comprising an effective amount of an antimicrobial polypeptide comprising Blad or an active variant thereof.

BRIEF DESCRIPTION OF THE DRAWINGS

FIG. 1 shows the *Lupinus albus* β-conglutin precursor encoding sequence (SEQ ID NO: 1); and FIG. 2 shows the internal fragment of the β-conglutin precursor encoding sequence that corresponds to Blad (SEQ ID NO: 3).

DETAILED DESCRIPTION OF THE INVENTION

The inventors have found that, when using a combination of a chelating agent and an antimicrobial agent that is effective against a plant pathogenic microorganism, said combination is particularly effective at inhibiting the growth of and/or killing a plant pathogenic microorganism. In one aspect, therefore, the inventors provide a composition comprising, or consisting essentially of, a chelating agent and an antimicrobial agent that is effective against a plant pathogenic microorganism. A composition comprising a chelating agent and an antimicrobial agent that is effective against a plant pathogenic microorganism may also be a formulation comprising another compound(s) added to the composition by the skilled person.

Antimicrobial Agents

The antimicrobial agent is any agent that reduces the growth of or kills a microorganism that is pathogenic to a plant. Said microorganism is preferably a bacterium (Gram-positive or Gram-negative) or a fungus, preferably a fungus (which may be a yeast or a mold). Preferably, the antimicrobial agent comprises (or consists essentially of) a polypeptide, such as an antifungal protein. Suitable examples of antifungal proteins include chitinases, chitin-binding proteins, chitosanases, β-1,3-glucanases, and β-N-acetyl-D-glucosaminidases. Particular examples of microorganisms that may be targeted by the antimicrobial agent are given below.

Blad Polypeptide

In preferred embodiments, where the antimicrobial agent comprises (or consists essentially of) a polypeptide, said polypeptide comprises (or consists essentially of) Blad or an active variant thereof.

Blad ("banda de *Lupinus albus* doce"—band from sweet *L. albus*) was the name given to a stable and intermediary breakdown product of β-conglutin, the major storage protein present in seeds of the *Lupinus* genus. It was characterised as a 20 kD polypeptide, composed of 173 amino acid residues, and encoded by an internal fragment (519 nucleotides, deposited in GenBank under the accession number ABB13526) of the gene encoding the precursor of β-conglutin from *Lupinus* (1791 nucleotides, published in GenBank, under the accession number AAS97865). When primers encoding Blad terminal sequences are used to amplify a sequence from genomic *Lupinus* DNA, a ~620 bp product is obtained, indicating the presence of an intron in the gene fragment encoding Blad. Naturally-occurring Blad is the main component of a 210 kD glycooligomer which accumulates exclusively (following intensive limited proteolysis of β-conglutin) in the cotyledons of *Lupinus* species, between days 4 and 12 after the onset of germination. Whilst said oligomer is glycosylated, naturally-occurring Blad is non-glycosylated. The Blad-containing glycooligomer is composed of several polypeptides, the major ones exhibiting molecular masses of 14, 17, 20, 32, 36, 48 and 50 kD. The 20 kD polypeptide, Blad, is by far the most abundant polypeptide within the oligomer and appears to be the only one with lectin activity. Naturally-occurring Blad constitutes approximately 80% of the total cotyledonary protein in 8-day old plantlets.

The *L. albus* β-conglutin precursor encoding sequence (SEQ ID NO: 1) is given in FIG. 13. The β-conglutin parent subunit coding sequence is located at residues 70 to 1668. The encoded, 533 amino acid residue β-conglutin parent subunit (SEQ ID NO: 2) is:

MGKMRVRFPTLVLVLGIVFLMAVSIGIAYGEKDVLKSHERPEEREQEEWQ

PRRQRPQSRREEREQEQEQGSPSYPRRQSGYERRQYHERSEQREEREQEQ

QQGSPSYSRRQRNPYHFSSQRFQTLYKNRNGKIRVLERFDQRTNRLENLQ

NYRIVEFQSKPNTLILPKHSDADYVLVVLNGRATITIVNPDRRQAYNLEY

GDALRIPAGSTSYILNPDDNQKLRVVKLAIPINNPGYFYDFYPSSTKDQQ

SYFSGFSRNTLEATFNTRYEEIQRIILGNEDEQEYEEQRRGQEQSDQDEG

-continued
VIVIVSKKQIQKLTKHAQSSSGKDKPSDSGPFNLRSNEPIYSNKYGNFYE

ITPDRNPQVQDLNISLTYIKINEGALLLPHYNSKAIYVVVVDEGEGNYEL

VGIRDQQRQQDEQEEKEEEVIRYSARLSEGDIFVIPAGYPISINASSNLR

LLGFGINADENQRNFLAGSKDNVIRQLDRAVNELTFPGSAEDIERLIKNQ

QQSYFANGQPQQQQQQQSEKEGRRGRRGSSLPF

The internal fragment of the β-conglutin precursor encoding sequence that corresponds to Blad (SEQ ID NO: 3) is given in FIG. 14. The Blad polypeptide (SEQ ID NO: 4) is:

RRQRNPYHFSSQRFQTLYKNRNGKIRVLERFDQRTNRLENLQNYRIVEFQ

SKPNTLILPKHSDADYVLVVLNGRATITIVNPDRRQAYNLEYGDALRIPA

GSTSYILNPDDNQKLRVVKLAIPINNPGYFYDFYPSSTKDQQSYFSGFSR

NTLEATFNTRYEEIQRIILGNED

Therefore, when the antimicrobial agent comprises (or consists essentially of) a polypeptide comprising (or consists essentially of) Blad or an active variant thereof, said agent comprises (or consists essentially of) a polypeptide sequence comprising (or consisting essentially of) of SEQ ID NO: 4 or an active variant thereof.

An active variant of Blad is a variant of Blad that retains the ability to act as an antimicrobial (i.e. has antimicrobial activity—see below for a description of the level of such activity and how to measure it). "An active variant of Blad" includes within its scope a fragment of SEQ ID NO: 4. In preferred embodiments, a fragment of SEQ ID NO: 4 is selected that is at least 10% of the length of SEQ NO: 4, preferably at least 20%, preferably at least 30%, preferably at least 40%, preferably at least 50%, preferably at least 60%, preferably at least 70%, preferably at least 80%, preferably at least 90% and most preferably at least 95% of the length of SEQ NO: 4. Blad or a variant thereof generally has a length of at least 10 amino acid residues, such as at least 20, 25, 30, 40, 50, 60, 80, 100, 120, 140, 160 or 173 amino acid residues.

"An active variant of Blad" also includes within its scope a polypeptide sequence that has homology with SEQ ID NO: 4, such as at least 40% identity, preferably at least 60%, preferably at least 70%, preferably at least 80%, preferably at least 85%, preferably at least 90%, preferably at least 95%, preferably at least 97%, and most preferably at least 99% identity, for example over the full sequence or over a region of at least 20, preferably at least 30, preferably at least 40, preferably at least 50, preferably at least 60, preferably at least 80, preferably at least 100, preferably at least 120, preferably at least 140, and most preferably at least 160 or more contiguous amino acid residues. Methods of measuring protein homology are well known in the art and it will be understood by those of skill in the art that in the present context, homology is calculated on the basis of amino acid identity (sometimes referred to as "hard homology").

The homologous active Blad variant typically differs from the polypeptide sequence of SEQ ID NO: 4 by substitution, insertion or deletion, for example from 1, 2, 3, 4, 5 to 8 or more substitutions, deletions or insertions. The substitutions are preferably 'conservative', that is to say that an amino acid may be substituted with a similar amino acid, whereby similar amino acids share one of the following groups: aromatic residues (F/H/W/Y), non-polar aliphatic residues (G/A/P/I/L/V), polar-uncharged aliphatics (C/S/T/M/N/Q)

and polar-charged aliphatics (D/E/K/R). Preferred subgroups comprise: G/A/P; I/L/V; C/S/T/M; N/Q; D/E; and K/R.

A polypeptide comprising Blad or an active variant thereof (as described above) may consist of Blad or an active variant thereof with any number of amino acid residues added to the N-terminus and/or the C-terminus provided that the polypeptide retains antimicrobial activity (again, see below for a description of the level of such activity and how to measure it). Preferably, no more than 300 amino acid residues are added to either or both ends of Blad or an active variant thereof, more preferably no more than 200 amino acid residues, preferably no more than 150 amino acid residues, preferably no more than 100 amino acid residues, preferably no more than 80, 60 or 40 amino acid residues, most preferably no more than 20 amino acid residues.

A polypeptide comprising (or consisting essentially of) Blad or an active variant thereof (as described above) may be utilised in the invention in the form of a purified (e.g. removed from a plant, animal or microbial source) or isolated form, and/or may be recombinant. Production of a recombinant form enables the production of active variants of Blad.

Methods of purifying naturally-occurring Blad are already described in the art (e.g. Ramos et al (1997) Planta 203(1): 26-34 and Monteiro et al (2010) PLoS ONE 5(1): e8542). A suitable source of naturally-occurring Blad is a plant of the *Lupinus* genus, such as *Lupinus albus*, preferably a cotyledon of said plant, preferably harvested between about 4 to about 14 days after the onset of germination, more preferably harvested 6 to 12 days after the onset of germination (such as 8 days after the onset of germination). Methods are disclosed in the art for a total protein extraction leading to a crude extract comprising Blad, and for a protein purification of such an extract leading to a partially purified extract e.g. comprising the Blad-containing glycooligomer that comprises Blad.

To isolate Blad itself one can then use SDS-PAGE and/or, preferably, reverse phase (RP)-HPLC on a C-18 column.

An alternative way of obtaining a partially purified extract comprising the glycooligomer that comprises Blad is to utilise the chitin binding activity of Blad. The glycooligomer binds in a very strong manner to a chitin column as part of a chitin affinity chromatography purification, being eluted with 0.05 N HCl. Details of an example of this purification method are as follows:

Cotyledons from eight-day old lupin plants were harvested and homogenized in Milli-Q plus water (pH adjusted to 8.0), containing 10 mM CaCl$_2$) and 10 mM MgCl$_2$. The homogenate was filtered through cheesecloth and centrifuged at 30,000 g for 1 h at 4° C. The pellet was subsequently suspended in 100 mM Tris-HCl buffer, pH 7.5, containing 10% (w/v) NaCl, 10 mM EDTA and 10 mM EGTA, agitated for 1 h at 4° C., and centrifuged at 30,000 g for 1 h at 4° C. The total globulin fraction, contained in the supernatant, was precipitated with ammonium sulphate (561 g/l), left stirring in the cold for 1 h and centrifuged at 30,000 g for 30 mM at 4° C. The pellet obtained was dissolved in 50 mM Tris-HCl buffer, pH 7.5, desalted in PD-10 columns equilibrated in the same buffer and passed through a chitin-affinity chromatography column pre-equilibrated in the same buffer. The column was washed with 50 mM Tris-HCl buffer, pH 7.5, and the bound proteins eluted with 0.05 N HCl. The eluted fractions were immediately neutralized with 2 M Tris and the peak fractions pooled, lyophilized and analyzed by SDS-PAGE.

For the preparation of the chitin column, crude chitin was obtained from Sigma and processed as follows: the chitin sample was washed extensively with Milli-Q plus water, followed by 0.05 N HCl. It was then washed with 1% (w/v) sodium carbonate and then with ethanol, until the absorbance of the wash was less than 0.05. Chitin was then packed into a pipette tip and equilibrated with 50 mM Tris-HCl buffer, pH 7.5.

Methods of producing recombinant proteins are well known in the art. Such methods as applied here will involve inserting the polynucleotide encoding a polypeptide comprising Blad or an active variant thereof into a suitable expression vector—enabling the juxtaposition of said polynucleotide with one or more promoters (e.g. an inducible promoter, such as T7lac) and with other polynucleotides or genes of interest—introducing the expression vector into a suitable cell or organism (e.g. *Escherichia coli*), expressing the polypeptide in the transformed cell or organism and removing the expressed recombinant polypeptide from that cell or organism. To assist such purification the expression vector may be constructed such that the polynucleotide additionally encodes, for example, a terminal tag that can assist purification: e.g., a tag of histidine residues for affinity purification. Once the recombinant polypeptide is purified, the purification tag may be removed from the polypeptide, e.g., by proteolytic cleavage.

In a composition of the invention that comprises an antimicrobial agent that comprises (or consists essentially of) a polypeptide, said polypeptide is preferably in partially purified form, more preferably in purified form. Said polypeptide is partially purified when it is present in an environment lacking one or more other polypeptides with which it is naturally associated and/or is represented by at least about 10% of the total protein present. Said polypeptide is purified when it is present in an environment lacking all, or most, other polypeptides with which it is naturally associated. For example, purified Blad means that Blad represents at least about 50%, at least about 60%, at least about 70%, at least about 75%, at least about 80%, at least about 85%, at least about 90%, at least about 95%, at least about 97%, at least about 98%, or at least about 99% of the total protein in a composition.

In a composition of the invention that comprises an antimicrobial agent, the *Lupinus* protein content may consist essentially of the Blad-containing glycooligomer that comprises a polypeptide that comprises (or consist essentially of) Blad or an active variant thereof.

Plant Pathogenic Microorganisms

The plant pathogenic microorganism against which the antimicrobial agent is effective is any microorganism capable of causing disease on or in a plant. Particularly preferred bacterial targets include pathogenic *Pseudomonas* species, such as *Pseudomonas aeruginosa, Pseudomonas syringae, Pseudomonas tolaasii* and *Pseudomonas agarici* (preferably *P. syringae*); pathogenic *Erwinia* species, such as *Erwinia persicina, Pectobacterium carotovorum, Erwinia amylovora, Erwinia chrysanthemi, Erwinia psidii* and *Erwinia tracheiphila*, and pathogenic *Streptomyces* species such as *Streptomyces griseus*.

Particularly preferred fungal targets include pathogenic *Alternaria* species, such as *Alternaria alternata, Alternaria arborescens, Alternaria arbusti, Alternaria brassicae, Alternaria brassicicola, Alternaria carotiincultae, Alternaria conjuncta, Alternaria dauci, Alternaria euphorbiicola,*

*Alternaria gaisen, Alternaria infectoria, Alternaria japonica, Alternaria petroselini, Alternaria selini, Alternaria solani* and *Alternaria smyrnii*, pathogenic *Fusarium* species, such as *Fusarium oxysporum* and *Fusarium graminearum* (preferably *F. oxysporum*); pathogenic *Botrytis* species, such as *Botrytis cinerea*; and pathogenic *Colletotrichum* species, such as *Colletotrichum actuatum, Colletotrichum coccodes, Colletotrichum capsici, Colletotrichum crassipes, Colletotrichum gloeosporioides, Colletotrichum graminicola, Colletotrichum kahawae, Colletotrichum lindemuthianum, Colletotrichum musae, Colletotrichum nigrum, Colletotrichum orbiculare, Colletotrichum pisi* and *Colletotrichum sublineolum.*

Chelating Agents

The chelating agent (also known as a chelant, a chelator or a sequestering agent) is any compound that binds to a metal ion to form a non-covalent complex and reduce the ion's activity. Suitable chelating agents include polyamino carboxylates, such as EDTA (ethylenediaminetetraacetic acid) and EGTA (ethyleneglycol bis(β-aminoethyl ether)-N,N,N',N'-tetraacetic acid). Preferably, EDTA is used as the chelating agent, preferably at a concentration of at least 10 µg/ml, at least 50 µg/ml, or at least 100 µg/ml, and up to 500 µg/ml, up to 1 mg/ml, up to 5 mg/ml, up to 10 mg/ml, or up to 20 mg/ml. Preferably, EDTA is used at a concentration of between 0.1 mg/ml and 20 mg/ml, more preferably between 1 mg/ml and 20 mg/ml.

Outcomes

The antimicrobial agent, in combination with the chelating agent, may be used to inhibit the growth of a plant pathogenic microorganism (meaning that it has microbistatic activity) and/or to kill said microorganism (meaning that it has microbicidal activity). The skilled person will be able to identify, through routine methods, a suitable dose and/or concentration of the antimicrobial agent, at a particular concentration of the selected chelating agent, to obtain a particularly desired growth inhibition or killing of the microorganism. Preferably, the combination of the antimicrobial agent and chelating agent is non-toxic to humans or animals.

Preferably, when a combination of the antimicrobial agent and chelating agent (e.g. a composition of the invention) is used as a microbistatic, the combination reduces the rate of growth by 10%, more preferably by 50%, more preferably by 75%, more preferably by 90%, more preferably by 95%, more preferably by 98%, more preferably by 99%, and even more preferably by 99.9% in comparison to equivalent conditions where the combination is not present. Most preferably the combination prevents any growth of the microorganism.

Preferably, when a combination of the antimicrobial agent and chelating agent (e.g. a composition of the invention) is used as a microbicidal, the combination kills 10% of the population of the microorganism, more preferably 50% of said population, more preferably 75% of said population, more preferably 90% of said population, more preferably 95% of said population, more preferably 98% of said population, more preferably 99% of said population, and even more preferably by 99.9% of said population in comparison to equivalent conditions where the combination is not present. Most preferably the combination kills all of the population of the microorganism.

When used to prevent or inhibit infection of a plant by a microorganism said combination is preferably used in an effective amount, that is to say an amount that provides a level of growth inhibition and/or killing of a microorganism such that a detectable level of infection prevention or inhibition is achieved (e.g. a detectable level of prevention or inhibition of plant tissue damage is achieved), preferably in comparison to equivalent conditions where the combination is not present.

If the antimicrobial chosen comprises a polypeptide comprising Blad or an active variant thereof then, in combination with a chelating agent (e.g. EDTA at any of the concentrations described above), suitable concentrations with which to use said polypeptide include at least 5 µg/ml, at least 10 µg/ml, at least 20 µg/ml, at least 50 µg/ml, at least 100 µg/ml or at least 500 µg/ml, and up to 1 mg/ml, up to 2.5 mg/ml, up to 5 mg/ml or up to 10 mg/ml. Preferably the concentration of said polypeptide is between 50 µg/ml and 10 mg/ml, more preferably between 500 µg/ml and 5 mg/ml, and even more preferably between 1 mg/ml and 5 mg/ml (such as about 2.5 mg/ml). For example, at 50 mM (i.e. about 15.8 mg/ml) EDTA a concentration of Blad of 1 mg/ml or 2.5 mg/ml can be used e.g. to inhibit the growth of *B. cinerea* or *F. oxysporum* respectively. This is a surprising finding given that Blad on its own needs to be used at about 5 mg/ml or 10 mg/ml (respectively) to inhibit the growth of these pathogens. The inventors' findings enable a) effective use of antimicrobial agents (that are effective against plant pathogens) at lower concentrations through the use of a chelating agent or b) increased efficacy of antimicrobial agents (that are effective against plant pathogens) at standard concentrations through the use of a chelating agent. This enables more economical/effective use of such antimicrobials to prevent or treat infection of a plant (or part thereof) by a microorganism.

Uses and Methods

The inventors also provide the use of a composition of the invention to inhibit the growth of and/or kill a plant pathogenic microorganism on a plant. To this end they also provide a method of inhibiting the growth of and/or killing a plant pathogenic microorganism comprising administering to a plant in need thereof a composition of the invention (e.g. an effective amount of said composition).

The inventors also provide the use of a chelating agent and an antimicrobial agent that is effective against a plant pathogenic microorganism to inhibit the growth of and/or kill a plant pathogenic microorganism on a plant. They also provide the use of a chelating agent to increase the activity of an antimicrobial that is effective against a plant pathogenic microorganism. To this end they also provide:

a) a method of inhibiting the growth of and/or killing a plant pathogenic microorganism comprising administering to a plant in need thereof a chelating agent and an antimicrobial agent that is effective against a plant pathogenic microorganism (e.g. an effective amount of a combination of said agents); and b) a method of increasing the activity of an antimicrobial that is effective against a plant pathogenic microorganism comprising using said antimicrobial with a chelating agent. In these embodiments said antimicrobial agent and said chelating agent may be administered to said plant as part of the same composition or separately. If these two agents are administered separately then the administration may be sequential (with either agent being administered first) or simultaneous. Administration to a plant may be achieved for example by applying (e.g. spraying) the agents (or composition comprising said agents) onto a plant (or any part thereof) or immersing the plant or part thereof (e.g. seed) in appropriate solution(s).

When a chelating agent is used to increase the activity of an antimicrobial that is effective against a plant pathogenic microorganism said chelating agent (and concentration thereof) is preferably selected such that the combination of said antimicrobial agent and said chelating agent provides an increased level of growth inhibition and/or killing of a plant pathogenic microorganism (e.g. such that an increased level of plant infection prevention or inhibition is achieved e.g. an increased level of prevention or inhibition of plant tissue damage is achieved), preferably in comparison to equivalent conditions where the chelating agent is not present.

In the use/method embodiments of the invention the antimicrobial agent and chelating agent are as described in detail above.

The plant in need of a combination of an antimicrobial that is effective against a plant pathogenic microorganism and a chelating agent may be any plant that is at risk of acquiring an infection or that has an infection, wherein said infection is caused by a plant pathogenic microorganism. Preferably, the plant is a crop plant (e.g. any plant that is grown to be harvested to provide food, livestock fodder, fuel, fibre, or any other commercially valuable product). Preferably, said crop plant is a food crop plant, such as a plant providing a sugar (e.g. sugar beet, sugar cane), a fruit (including a nut), a vegetable or a seed. Particular plants that provide seeds include cereals (e.g. maize, wheat, barley, sorghum, millet, rice, oats and rye) and legumes (e.g. beans, peas and lentils).

The inventors also provide the use of a composition comprising (or consisting essentially of) an antimicrobial polypeptide comprising (or consisting essentially of) Blad or an active variant thereof to kill, or inhibit the growth of, a plant pathogenic bacterium on a plant. To this end the inventors further provide a method of killing, or inhibiting the growth of, a plant pathogenic bacterium on a plant, said method comprising administering to said plant a composition comprising (or consisting essentially of) an effective amount of an antimicrobial polypeptide comprising (or consisting essentially of) Blad or an active variant thereof. Optionally the antimicrobial polypeptide comprising (or consisting essentially of) Blad or an active variant thereof may be used in isolated form.

In preferred embodiments, said composition is applied to a plant in need thereof. The plant in need of said composition may be any plant that is at risk of acquiring an infection or that has an infection, wherein said infection is caused by a plant pathogenic bacterium. Preferred plants are as described above. The meanings of 'killing/inhibiting growth of a bacterium', and 'effective amount', are as described above in relation to the combination of antimicrobial agent and chelating agent.

EXAMPLES

In the following Examples BLAD denotes the naturally-occurring Blad-containing glycooligomer comprising the 20 kD Blad polypeptide, purified as per Ramos et al (1997) Planta 203(1): 26-34: see "Plant material and growth conditions" and "Purification of proteins" parts of the Materials and Methods section of that document.

Definitions

MIC—Minimum Inhibitory Concentration: the lowest concentration of an antimicrobial that inhibits the visible growth of a microorganism.

MFC/MBC—Minimum Fungicidal/Bactericidal Concentration (or Minimal Lethal Concentration): the lowest concentration of an antimicrobial agent needed to kill 99.9% of the initial inoculum after 24 h under a standardized set of conditions.

Example 1—Bactericidal Activity of BLAD and Synergistic Effect of EDTA Thereon

A. BLAD was found to be bacteriostatic at 100 µg/ml and bactericidal at 250 µg/ml against *P. aeruginosa*. Against *P. aeruginosa* BLAD at 50 µg/ml or EDTA at 1 mg/ml inhibits growth (i.e. both are bacteriostatic) but a combination of the two is bactericidal.

B. Against *Erwinia pirsicina* BLAD has an MIC of 32 µg/ml and EDTA has an MIC of 15 mM. However, in the presence of sub-inhibitory amounts of EDTA (0.75 mM) the MIC for BLAD is lowered to 16 µg/ml.

C. Against *Streptomyces griseus* BLAD has an MIC of 1024 µg/ml and EDTA has an MIC of 16 mM. However, in the presence of sub-inhibitory amounts of EDTA (8 mM) the MIC for BLAD is lowered to 256 µg/ml.

Example 2—Synergistic Effect of EDTA on Fungicidal Activity of BLAD

Inhibition Halo Data for BLAD with and without EDTA Against *Botrytis cinerea* on Potato Dextrose Agar (PDA) at 1.2% w/v of Agar (Incubation 3 Days at 25° C.):

| Agent(s) | Inhibition halo diameter (mm) | | | Average inhibition halo diameter (mm) |
|---|---|---|---|---|
| Blad (200 µg) | 21 | 21 | 22 | 21 |
| Blad (100 µg) | 16 | 16 | 15 | 16 |
| Blad (50 µg) | 0 | 0 | 0 | 0 |
| Blad (20 µg) | 0 | 0 | 0 | 0 |
| EDTA (50 nnM) | 0 | 0 | 0 | 0 |
| Blad (200 µg) + EDTA (50 nnM) | 23 | 24 | 25 | 24 |
| Blad (100 µg) + EDTA (50 nnM) | 19 | 19 | 18 | 19 |
| Blad (50 µg) + EDTA (50 nnM) | 13 | 15 | 14 | 14 |
| Blad (20 µg) + EDTA (50 nnM) | 10 | 12 | 12 | 11 |

Growth of *B. cinera* was inhibited with 200 µg and 100 µg of BLAD. This inhibition was potentiated with the addition of 50 mM (approximately 15.8 mg/ml) EDTA.

No growth inhibition was observed using BLAD alone at 20 µg or 50 µg or using EDTA alone at 50 mM. However, inhibition was observed when BLAD at either concentration was combined with 50 mM EDTA.

Inhibition Halo Data for BLAD with and without EDTA Against *Fusarium oxysporum* on Potato Dextrose Agar (PDA) at 1.2% w/v of Agar (Incubation 3 Days at 25° C.):

| Agent(s) | Inhibition halo diameter (mm) | | | Average inhibition halo diameter (mm) |
|---|---|---|---|---|
| Blad (200 µg) | 25 | 22 | 22 | 23 |
| Blad (100 µg) | 0 | 0 | 0 | 0 |
| Blad (50 µg) | 0 | 0 | 0 | 0 |
| Blad (20 µg) | 0 | 0 | 0 | 0 |
| EDTA (50 nnM) | 0 | 0 | 0 | 0 |
| Blad (200 µg) + EDTA (50 nnM) | 28 | 27 | 30 | 28 |
| Blad (100 µg) + EDTA (50 nnM) | 22 | 21 | 26 | 23 |
| Blad (50 µg) + EDTA (50 nnM) | 24 | 20 | 15 | 20 |
| Blad (10 µg) + EDTA (50 nnM) | 0 | 0 | 0 | 0 |

Growth of *F. oxysprum* was inhibited with 200 µg of BLAD. This inhibition was potentiated with the addition of 50 mM EDTA.

No growth inhibition was observed using BLAD alone at 20 μg, 50 μg or 100 μg, or using EDTA alone at 50 mM. However, inhibition was observed when 50 μg or 100 μg of BLAD was combined with 50 mM EDTA.

The invention claimed is:

1. A method for treating a plant infected with *Alternaria solani*, comprising administering to the infected plant a composition comprising a Blad polypeptide comprising the amino acid sequence of SEQ ID NO: 4 at a concentration of between 20 µg/mL and 50 µg/mL, and EDTA at a concentration of 50 mM, wherein the combined concentrations are effective to kill *Alternaria solani*.

2. A method for treating a plant infected with *Alternaria alternata*, comprising administering to the infected plant a composition comprising a Blad polypeptide comprising the amino acid sequence of SEQ ID NO: 4 at a concentration of 50 µg/mL and 100 µg/mL, and EDTA at a concentration of 50 mM, wherein the combined concentrations are effective to kill *Alternaria alternata*.

* * * * *

```
                       SEQUENCE LISTING

<160> NUMBER OF SEQ ID NOS: 4

<210> SEQ ID NO 1
<211> LENGTH: 1791
<212> TYPE: DNA
<213> ORGANISM: Lupinus albus

<400> SEQUENCE: 1
gatggcgatg aatgaacact gcgtttgctg gctttgatga aaatcgagtg caacctaata      60
taatcaaata tgggtaagat gagagtgagg tttccaacgt tagtgttggt actaggaata     120
gtattcctca tggcagtgtc aattggtatt gcttatggag aaaaagatgt gctaaagagt     180
catgagaggc ctgaggaaag agaacaagag gagtggcaac ctaggagaca acgacctcaa     240
agtagaaggg aagagagaga gcaagagcaa gagcagggtt ctccctcata cccacgcagg     300
cagagtggtt atgagaggag acaataccat gagaggagtg agcagaggga agagagagag     360
caagaacaac aacaaggttc tccctcatac tcacgtagac aaaggaaccc ttatcacttc     420
agctctcaaa gattccaaac tctttacaaa aataggaatg gcaaaatccg tgtgctcgag     480
aggtttgacc aaagaaccaa tagacttgag aatctccaaa actaccgcat tgttgagttc     540
caatcaaaac ctaacactct cattctccct aaacactctg atgctgacta cgtcctcgtt     600
gtactcaatg gtagagccac aatcacgata gtaaaccctg atagaagaca agcatataac     660
cttgagtatg gcgatgctct cagaatccca gctggctcaa cttcatatat ccttaacccg     720
gatgacaacc agaagcttag agtagtcaag ctcgcaatac ccatcaacaa tcctggctac     780
ttttatgatt tctatccatc gagtactaaa gaccaacaat cctacttcag tggcttcagc     840
aggaacactt tagaggccac cttcaatact cgttatgaag agatacaaag gattatttta     900
gggaatgagg atgagcaaga atatgaggaa caaaggcgtg gcaagagca gagcgaccaa     960 gacgaggggg tgatagtgat agtttcaaag aaacagatcc aaaaattgac aaaacacgct    1020
caatcttcat caggaaaaga caaaccctct gattctggcc ccttcaactt gagaagcaat    1080
gagcccatat attcaaacaa gtatgggaac ttctatgaaa tcactccaga tagaaaccct    1140
caagttcagg atttgaatat ctctctcacc tatataaaaa ttaacgaggg agctttgttg    1200
ttgccacact ataactcaaa ggccatatat gtagtcgtgg ttgatgaagg agaaggaaat    1260
tatgaactgg taggtattcg agatcaacaa cgacaacaag atgagcaaga agagaaagag    1320
gaagaagtga taggtatag tgctagatta tcagaaggtg acattttgt aattccagca      1380 ggttatccaa tttccatcaa tgcttcctca aatcttcgct tgcttggatt tggcatcaat    1440
gctgatgaaa accagaggaa tttcctcgca ggttctaaag acaatgtgat aaggcagtta    1500
gatagagcag tgaatgagct cacattccct ggttctgctg aagatattga gagattaatc    1560
aaaaaccaac aacagtcttca ctttgcaaat ggtcagcctc aacaacaaca acaacaacaa    1620
agtgagaagg agggaaggcg tggaagaagg ggttcatctc ttccattttg agcactttt    1680 actaagctgt tttaaaagct actatcatgt aagagctcat agtgagctac tgagagaata    1740
ataaaactaa agttggacct ttgtactaat aatgttaata aaaaaaaaa a             1791

<210> SEQ ID NO 2
<211> LENGTH: 533
<212> TYPE: PRT
<213> ORGANISM: Lupinus albus
```

<400> SEQUENCE: 2

```
Met Gly Lys Met Arg Val Arg Phe Pro Thr Leu Val Leu Val Leu Gly
1               5                   10                  15

Ile Val Phe Leu Met Ala Val Ser Ile Gly Ile Ala Tyr Gly Glu Lys
            20                  25                  30

Asp Val Leu Lys Ser His Glu Arg Pro Glu Arg Glu Gln Glu Glu
        35                  40                  45

Trp Gln Pro Arg Arg Gln Arg Pro Gln Ser Arg Arg Glu Glu Arg Glu
    50                  55                  60

Gln Glu Gln Glu Gln Gly Ser Pro Ser Tyr Pro Arg Arg Gln Ser Gly
65                  70                  75                  80

Tyr Glu Arg Arg Gln Tyr His Glu Arg Ser Glu Gln Arg Glu Glu Arg
                85                  90                  95

Glu Gln Glu Gln Gln Gln Gly Ser Pro Ser Tyr Ser Arg Arg Gln Arg
                100                 105                 110

Asn Pro Tyr His Phe Ser Ser Gln Arg Phe Gln Thr Leu Tyr Lys Asn
                115                 120                 125

Arg Asn Gly Lys Ile Arg Val Leu Glu Arg Phe Asp Gln Arg Thr Asn
            130                 135                 140

Arg Leu Glu Asn Leu Gln Asn Tyr Arg Ile Val Glu Phe Gln Ser Lys
145                 150                 155                 160

Pro Asn Thr Leu Ile Leu Pro Lys His Ser Asp Ala Asp Tyr Val Leu
                165                 170                 175

Val Val Leu Asn Gly Arg Ala Thr Ile Thr Ile Val Asn Pro Asp Arg
            180                 185                 190

Arg Gln Ala Tyr Asn Leu Glu Tyr Gly Asp Ala Leu Arg Ile Pro Ala
        195                 200                 205

Gly Ser Thr Ser Tyr Ile Leu Asn Pro Asp Asp Asn Gln Lys Leu Arg
    210                 215                 220

Val Val Lys Leu Ala Ile Pro Ile Asn Asn Pro Gly Tyr Phe Tyr Asp
225                 230                 235                 240

Phe Tyr Pro Ser Ser Thr Lys Asp Gln Gln Ser Tyr Phe Ser Gly Phe
                245                 250                 255

Ser Arg Asn Thr Leu Glu Ala Thr Phe Asn Thr Arg Tyr Glu Glu Ile
            260                 265                 270

Gln Arg Ile Ile Leu Gly Asn Glu Asp Glu Gln Glu Tyr Glu Glu Gln
        275                 280                 285

Arg Arg Gly Gln Glu Gln Ser Asp Gln Asp Glu Gly Val Ile Val Ile
    290                 295                 300

Val Ser Lys Lys Gln Ile Gln Lys Leu Thr Lys His Ala Gln Ser Ser
305                 310                 315                 320

Ser Gly Lys Asp Lys Pro Ser Asp Ser Gly Pro Phe Asn Leu Arg Ser
                325                 330                 335

Asn Glu Pro Ile Tyr Ser Asn Lys Tyr Gly Asn Phe Tyr Glu Ile Thr
            340                 345                 350

Pro Asp Arg Asn Pro Gln Val Gln Asp Leu Asn Ile Ser Leu Thr Tyr
        355                 360                 365

Ile Lys Ile Asn Glu Gly Ala Leu Leu Leu Pro His Tyr Asn Ser Lys
    370                 375                 380

Ala Ile Tyr Val Val Val Asp Glu Gly Glu Gly Asn Tyr Glu Leu
385                 390                 395                 400

Val Gly Ile Arg Asp Gln Gln Arg Gln Gln Asp Glu Gln Glu Glu Lys
                405                 410                 415
```

Glu Glu Glu Val Ile Arg Tyr Ser Ala Arg Leu Ser Glu Gly Asp Ile
            420                 425                 430

Phe Val Ile Pro Ala Gly Tyr Pro Ile Ser Ile Asn Ala Ser Ser Asn
            435                 440                 445

Leu Arg Leu Leu Gly Phe Gly Ile Asn Ala Asp Glu Asn Gln Arg Asn
450                 455                 460

Phe Leu Ala Gly Ser Lys Asp Asn Val Ile Arg Gln Leu Asp Arg Ala
465                 470                 475                 480

Val Asn Glu Leu Thr Phe Pro Gly Ser Ala Glu Asp Ile Glu Arg Leu
            485                 490                 495

Ile Lys Asn Gln Gln Gln Ser Tyr Phe Ala Asn Gly Gln Pro Gln Gln
            500                 505                 510

Gln Gln Gln Gln Gln Ser Glu Lys Glu Gly Arg Arg Gly Arg Arg Gly
            515                 520                 525

Ser Ser Leu Pro Phe
            530

<210> SEQ ID NO 3
<211> LENGTH: 519
<212> TYPE: DNA
<213> ORGANISM: Lupinus albus

<400> SEQUENCE: 3
cgtagacaaa ggaacccta tcacttcagc tctcaaagat ccaaactct ttacaaaaat     60 aggaatggca aaatccgtgt gctcgagagg tttgaccaaa gaaccaatag acttgagaat    120
ctccaaaact accgcattgt tgagttccaa tcaaaaccta cactctcat tctccctaaa    180 cactctgatg ctgactacgt cctcgttgta ctcaatggta gagccacaat cacgatagta    240
aaccctgata aagacaagc atataacctt gagtatggcg atgctctcag aatcccagct    300
ggctcaactt catatatcct taacccggat gacaaccaga gcttagagt agtcaagctc    360 gcaataccca tcaacaatcc tggctacttt tatgatttct atccatcgag tactaaagac    420
caacaatcct acttcagtgg cttcagcagg aacacttag aggccacctt caatactcgt    480
tatgaagaga tacaaaggat tattttaggg aatgaggat                           519

<210> SEQ ID NO 4
<211> LENGTH: 173
<212> TYPE: PRT
<213> ORGANISM: Lupinus albus

<400> SEQUENCE: 4

Arg Arg Gln Arg Asn Pro Tyr His Phe Ser Ser Gln Arg Phe Gln Thr
1               5                   10                  15

Leu Tyr Lys Asn Arg Asn Gly Lys Ile Arg Val Leu Glu Arg Phe Asp
            20                  25                  30

Gln Arg Thr Asn Arg Leu Glu Asn Leu Gln Asn Tyr Arg Ile Val Glu
            35                  40                  45

Phe Gln Ser Lys Pro Asn Thr Leu Ile Leu Pro Lys His Ser Asp Ala
    50                  55                  60

Asp Tyr Val Leu Val Leu Asn Gly Arg Ala Thr Ile Thr Ile Val
65                  70                  75                  80

Asn Pro Asp Arg Arg Gln Ala Tyr Asn Leu Glu Tyr Gly Asp Ala Leu
            85                  90                  95

Arg Ile Pro Ala Gly Ser Thr Ser Tyr Ile Leu Asn Pro Asp Asp Asn
            100                 105                 110

```
                                -continued

Gln Lys Leu Arg Val Val Lys Leu Ala Ile Pro Ile Asn Asn Pro Gly
        115                 120                 125

Tyr Phe Tyr Asp Phe Tyr Pro Ser Ser Thr Lys Asp Gln Gln Ser Tyr
    130                 135                 140

Phe Ser Gly Phe Ser Arg Asn Thr Leu Glu Ala Thr Phe Asn Thr Arg
145                 150                 155                 160

Tyr Glu Glu Ile Gln Arg Ile Ile Leu Gly Asn Glu Asp
                165                 170
```